United States Patent [19]

Berner et al.

[11] Patent Number: 4,952,620
[45] Date of Patent: Aug. 28, 1990

[54] PHOTOLYTICALLY CLEAVABLE N-ACYLATED STERICALLY HINDERED AMINES

[75] Inventors: Godwin Berner, Binningen; Mario Slongo, Tafers, both of Switzerland

[73] Assignee: Ciba-Geigy Corporation, Ardsley, N.Y.

[21] Appl. No.: 231,315

[22] Filed: Aug. 12, 1988

Related U.S. Application Data

[62] Division of Ser. No. 899,133, Aug. 21, 1986, Pat. No. 4,785,102.

[30] Foreign Application Priority Data

Aug. 27, 1985 [CH] Switzerland ............... 3668/85

[51] Int. Cl.$^5$ ............................................. C08K 5/34
[52] U.S. Cl. ......................................... 524/99; 521/91; 521/96; 521/97; 521/100; 521/102; 521/103
[58] Field of Search ............... 524/96, 97, 100, 102, 524/103, 98, 99, 91

[56] References Cited

U.S. PATENT DOCUMENTS

| | | | |
|---|---|---|---|
| 4,283,686 | 9/1981 | Rody et al. | 546/20 |
| 4,344,876 | 8/1982 | Berner | 524/91 |
| 4,517,283 | 5/1985 | Leppard et al. | 430/512 |
| 4,552,885 | 11/1985 | Gabriele et al. | 514/316 |
| 4,578,454 | 3/1986 | Cantatore | 524/103 |
| 4,687,800 | 8/1987 | Nelson et al. | 524/103 |
| 4,689,360 | 8/1987 | Nelson et al. | 524/103 |
| 4,690,963 | 9/1987 | Nelson et al. | 524/103 |
| 4,691,015 | 9/1987 | Behrens et al. | 546/20 |
| 4,692,486 | 9/1987 | Gugumus | 524/100 |
| 4,701,485 | 10/1987 | Nelson et al. | 524/103 |
| 4,710,527 | 12/1987 | Nelson et al. | 524/103 |
| 4,774,332 | 9/1988 | Avar | 524/103 |
| 4,780,494 | 10/1988 | Hess et al. | 524/100 |
| 4,804,699 | 2/1989 | Nelson et al. | 524/103 |

FOREIGN PATENT DOCUMENTS 2163158 2/1986 United Kingdom .

OTHER PUBLICATIONS

Kurumada et al: "Photostabilizing Activity of N-Acylated Hindered Amine", J. Polymer Science: Phy. Chem. Ed., 23, 2347–2756 (1985).
CA, 103: 96306y.
Cabre Castellvi et al: *Snythesis*, pp. 616–620, Aug. 1981.
P. Klemchuk et al: *Polymer Degradation and Stability*, 22, 241–274 (1988).
Berger et al: *Developments in Polymer Stabilization*, 6, pp. 1–27 (1983).
W. Ya Shylapintokh et al: *Developments in Polymer Stabilization*, 5, 41–70 (1982).
CA, 99: 100958f.
CA, 97: 73998u.
CA, 100: 104558u.
Moffet et al., J. of Am. Chem. Soc., vol. 82, pp. 1600–1607 (1960).

*Primary Examiner*—Veronica P. Hoke
*Attorney, Agent, or Firm*—JoAnn Villamizar; Harry Falber

[57] ABSTRACT

Sterically hindered cyclic amines which are substituted by a photoactivatable acyl group at the basic nitrogen atom can be deacylated by irradiation with UV light. This is advantageous if the basicity of the amines proves troublesome during application. Examples of such photoactivatable acyl groups are phenylglyoxyl, phenylacetyl or naphthylacetyl groups.

6 Claims, No Drawings

PHOTOLYTICALLY CLEAVABLE N-ACYLATED STERICALLY HINDERED AMINES

This is a divisional of application Ser. No. 899,133 filed on Aug. 21, 1986, now U.S. Pat. No. 4,785,102.

The present invention relates to photolytically cleavable, N-acylated sterically hindered amines and to the use thereof for stabilising polymers against light-induced damage, in particular for stabilizing acid curable resins.

It is known that sterically hindered amines are effective light stabilisers for polymers. Particular importance attaches to the light protection of varnishes for producing industrial finishes of which a long service life is required, e.g. automotive finishes or machine finishes. Acid-catalysed stoving varnishes are often used for obtaining such finishes. The addition of acid curing catalysts as well as amine light stabilisers to such varnishes before curing may result in unwanted interactions of both these components. This problem can be overcome by using N-acylated piperidines as "amine light stabilisers" in accordance with the teaching of European patent application EP-A-52 073. These compounds are no longer basic and thus do not give rise to interactions with acid catalysts. However, the light protective action of the N-acylated piperidines is usually inferior to that of the analogous N-unsubstituted or N-alkylated piperidines. The problem was therefore to provide light stabilisers which do not undergo interaction with the acid catalyst and which induce in the cured varnish as good a light-stabilizing effect as the N-unsubstituted or N-alkylated amine light stabilisers. The same consideration also applies to acid curable resins, aside from their utility as varnishes.

It has been found that this problem can be solved by using N-acylated, sterically hindered amines as light stabilisers, which amines can be cleaved by photolysis and converted into N-unsubstituted amine light stabilisers after curing the resin by irradiation. These photolytically curable amine light stabilisers are so far not known in the art and therefore had to be developed specially for this purpose.

Accordingly, the invention relates to compounds of formula I

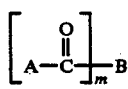
(I)

wherein
m is 1, 2 or 3,
A is a $R^1$—CO— or $R^2$—CH$_2$— group, wherein
$R^1$ is phenyl or phenyl which is substituted by halogen, $C_1$–$C_{12}$alkyl, $C_1$–$C_4$alkoxy or hydroxy, or is naphthyl, $C_1$–$C_{12}$alkoxy, cyclohexyloxy, phenoxy or benzyloxy and, if m=1, may also be a radical B,
$R^2$ is halogen, phenyl, naphthyl, —CN, —P(O)(OR$^3$)$_2$, —CH$_3$CO— or —OR$^4$,
wherein
$R^3$ is $C_1$–$C_4$alkyl or phenyl, and
$R^4$ is phenyl or phenyl which is substituted by halogen or $C_1$–$C_4$-alkyl, and
B is a radical of valency m of a sterically hindered cyclic amine which is attached to the A—CO— radical through the sterically hindered nitrogen atom.

The cyclic amine radical B can be a 5-, 6- or 7-membered ring which may also contain other hetero atoms in addition to the basic nitrogen atom. However, the radical B is not an aromatic heterocyclic radical. In particular, where m=1, B may be a radical of formula

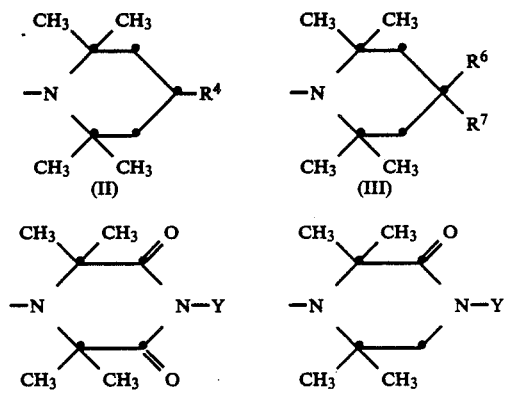

wherein
$R^5$ is hydrogen, —OR$^8$,

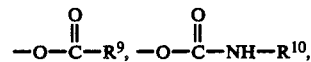

—N(R$^{10}$R$^{11}$),
$R^6$ is —OH or —OR$^{12}$ and $R^7$ is —OR$^{12}$, —CN, —COOR$^{13}$ or —CONH$_2$, or $R^6$ and $R^7$ together are the oxo radical (=O), or $R^6$ and $R^7$, together with the C-atom to which they are attached, form a heterocyclic spiro ring which may be a 2-spiro-1,3-dioxolane, 2-spiro-1,3-dioxane, 5-spiro-1,3-oxazolidine, 2-spiro-1,3-oxazolidine or 5-spiro-1,3-imidazolidine ring and which may be substituted by one or more identical or different members selected from alkyl, substituted alkyl, alkylene and/or the oxo radical,
$R^8$ is $C_1$–$C_2$alkyl, benzyl, allyl or 2-cyanoethyl,
$R^9$ is $C_1$–$C_{18}$alkyl, $C_2$–$C_{12}$alkenyl, $C_5$–$C_8$cycloalkyl, phenyl or phenyl which is substituted by halogen, $C_1$–$C_{12}$alkyl, $C_1$–$C_4$alkoxy and/or hydroxyl, or is $C_7$–$C_{12}$phenylalkyl, $C_1$–$C_4$alkoxy or phenoxy,
$R^{10}$ is $C_1$–$C_{12}$alkyl, cyclohexyl, phenyl, naphthyl, or phenyl which is substituted by $C_1$–$C_4$alkyl,
$R^{11}$ is $C_2$–$C_{12}$alkanoyl, $C_3$–$C_8$alkenoyl, benzoyl or a group of the formula

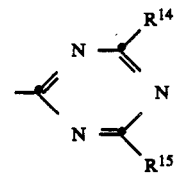

wherein $R^{14}$ and $R^{15}$ are each independently of the other $C_1$–$C_8$alkoxy, phenoxy, or a group —N(R$^{10}$)(R$^{16}$), in which $R^{16}$ is hydrogen or $C_1$–$C_{12}$alkyl,
$R^{12}$ is $C_1$–$C_{12}$alkyl and $R^{13}$ is $C_1$–$C_4$alkyl, and
Y is hydrogen, $C_1$–$C_{12}$alkyl, allyl or benzyl.
Where m is 2, B may in particular be a divalent radical selected from:

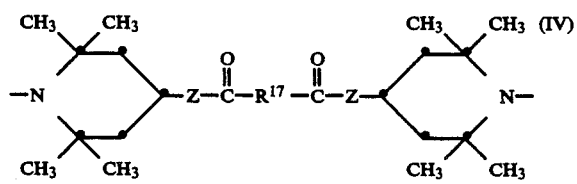

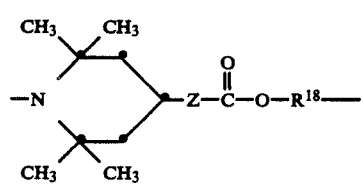

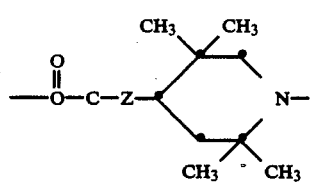

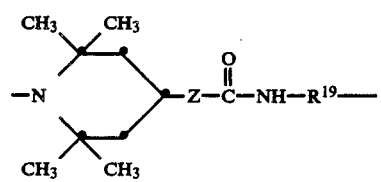

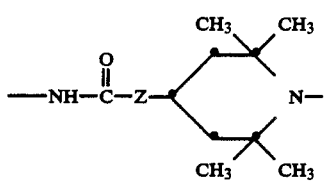

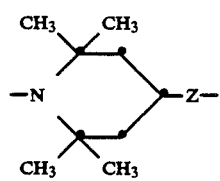

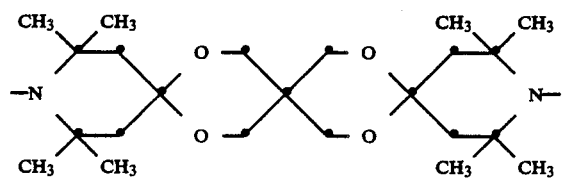

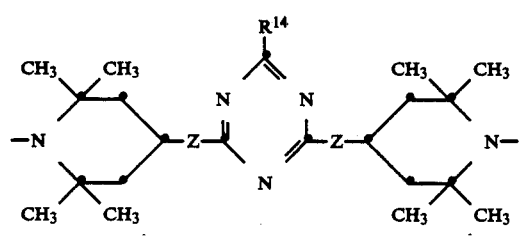

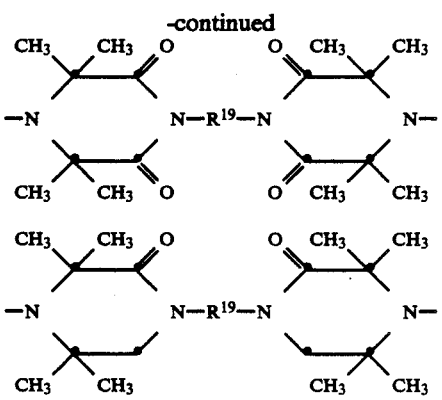

wherein
Z is —O—, —NH— or —NR$^{10}$,
R$^{17}$ is a divalent aliphatic, cycloaliphatic or aromatic radical of 1 to 20 carbon atoms or a radical —NH—R$^{19}$—NH—,
R$^{18}$ is a divalent aliphatic or cycloaliphatic or aromatic radical of 2 to 12 carbon atoms,
R$^{19}$ is a divalent aliphatic, cycloaliphatic or aromatic radical of 2 to 16 carbon atoms, and
R$^{10}$ and R$^{14}$ are as previously defined.
Where m=3, B may be in particular a trivalent radical of formula

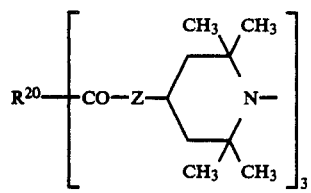

wherein R$^{20}$ is a trivalent aliphatic radical of 3 to 8 carbon atoms or a trivalent aromatic radical of 6 to 10 carbon atoms, R$^{21}$ is a 1,3,5-triazin-2,4,6-triyl radical, and Z is as previously defined.

Substituents defined above as alkyl may be unbranched or branched alkyl. R$^3$ and R$^{13}$ as C$_1$–C$_4$alkyl are methyl, ethyl, n-propyl, isopropyl, n-butyl, sec-butyl isobutyl or tert-butyl. R$^8$, R$^{10}$, R$^{12}$, R$^{16}$ and Y as C$_1$–C$_{12}$alkyl may be pentyl, n-hexyl, 2-ethylbutyl, n-octyl, 2-ethyl-n-hexyl, n-nonyl, isodecyl or n-dodecyl. R$^9$ as C$_1$–C$^{18}$alkyl may be tetradecyl, hexadecyl or octadecyl.

R$^9$ as C$_2$–C$_{12}$alkyl may be vinyl, allyl, 2-propenyl, methallyl, 2-buten-1-yl, 2-buten-2-yl, 2-hexen-1-yl, 2-octen-1-yl or 10-un-decen-1-yl.

R$^9$ as C$_5$–C$_6$cycloalkyl may be cyclopentyl, cyclohexyl, methylcyclohexyl or cyclooctyl. R$^9$ as C$_7$–C$_{12}$-phenylalkyl may be benzyl, 1- or 2-phenylethyl or 3-phenylpropyl.

R$^1$, R$^4$ and R$^9$ as substituted phenyl radicals may be 4-chlorophenyl, 3-bromophenyl, 2-fluorophenyl, 4-methylphenyl, 2,4-dimethylphenyl, 4-tert-butylphenyl, 3-methoxyphenyl or 4-ethoxyphenyl. R$^1$ and R$^9$ may also be 4-octylphenyl, 4-dodecylphenyl, 4-hydroxyphenyl, 2-methyl-4-hydroxyphenyl or 3,5-di-(tert-butyl)-4-hydroxyphenyl.

R$^9$, R$^{14}$ and R$^{15}$ as alkoxy radicals may be methoxy, ethoxy or butoxy. R$^{14}$ and R$^{15}$ may also be hexyloxy, octyloxy, decyloxy or dodecyloxy.

$R^{11}$ as alkanoyl or alkenoyl may be acetyl, propionyl, butyroyl, hexanoyl, octanoyl, lauroyl, acryloyl, methacryloyl or crotonoyl.

$R^{17}$ as a divalent aliphatic, cycloaliphatic or aromatic radical may be methylene, 1,2-ethylene or $C_3$-$C_{20}$polymethylene; or branched $C_3$-$C_{20}$alkylene such as 1,2-propylene or trimethyltetramethylene; or $C_2$-$C_{10}$alkenylene such as vinylene or 2-buten-1,4-ylene; or cycloalkylene such as 1,4-cyclohexylene or 1,3-cyclohexylene; or cycloalkane-dialkylene such as cyclohexane-1,4-dimethylene; or arylene such as 1,3- or 1,4-phenylene, 1,4- or 1,5-naphthylene, 4,4'-diphenylene, diphenylmethane-4,4'-diyl or diphenyl oxide-4,4'-diyl; or aralkylene such as m- or p-xylene.

$R^{18}$ as a divalent aliphatic, cycloaliphatic or aromatic radical is preferably a radial of 2 to 8 carbon atoms. Examples of such radicals are 1,2-ethylene, 1,2-propylane, 1,3-propylene, 1,2-butylene, 1,4-butylene, hexamethylene, 1,4-cyclohexylene or cyclohexane-1,4-dimethylene.

$R^{19}$ as a divalent aliphatic, cycloaliphatic or aromatic radical may be an unbranched or branched alkylene radical such as 1,2-ethylene, trimethylene, tetramethylene, hexamethylene, octamethylene, dodecamethylene, 2,2-dimethyltrimethylene or trimethyloctamethylene; or a cycloalkylene radical such as 1,4-cyclohexylene; or cycloalkanealkylene such as cyclohexane-1,4-dimethylene; or arylene such as 1,3-phenylene, 4,4'-diphenylene, diphenylmethane-4,4'-diyl or diphenyl oxide-4,4'-diyl; or arene-dialkylene such as m- or p-xylylene.

$R^{20}$ as a trivalent aliphatic or aromatic radical may be propane-1,2-3-triyl, butane-1,2,4-triyl, benzene-1,3,5-triyl, benzene-1,2,4-triyl or naphthalene-1,4,5-triyl.

Preferred compounds of formula I are those wherein A is a $R^1$—CO— or $R^2$—$CH_2$— group, wherein $R^1$ is phenyl or phenyl which is substituted by halogen, $C_1$-$C_{12}$alkyl or $C_1$-$C_4$alkoxy, or is unsubstituted naphthyl, and $R^2$ is phenyl, naphthyl, —CN or $CH_3CO$—.

Particularly preferred compounds of formula I are those wherein A is a benzoyl group or an o-naphthylmsthyl group. Further preferred compounds of formula I are those wherein m is 1 or 2 and B is a group of formulae II, III or IV.

Where m=1 and A is B—CO, the compounds conform to the formula B—CO—CO—B, wherein both radicals B are attached to the —CO group through their sterically hindered nitrogen atoms. The compounds of formula I can be prepared in principle from the N-unsubstituted amines

by reaction with the corresponding carboxylic acid chlorides A—COCl or anhydrides $(A—CO)_2O$. The compounds B—CO—CO—B can be prepared by reaction of 2 moles of H-B with 1 mole of oxalyl chloride. The N-unsubstituted sterically hindered cyclic amines are known compounds which have been described in a number of patent specifications, for example U.S. patent specifications Nos. 3,640,928, 3,790,525 and 3,639,409.

Some of the acid chlorides A—COCl are known compounds or can be prepared from the corresponding carboxylic acids by known methods, for example by reaction with thionyl chloride. Some of the anhydrides are also known and can be prepared e.g. by the method described by J. Cabre-Castelvi et al., in Synthesis, 1981, 616.

Representative examples of individual compounds of formula I are listed below. In these compounds,

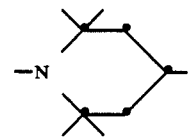

denotes a 2,2,6,6-tetramethylpiperidine radical
Ph- is a phenyl radical and
Naphth- is an α-naphthyl radical.

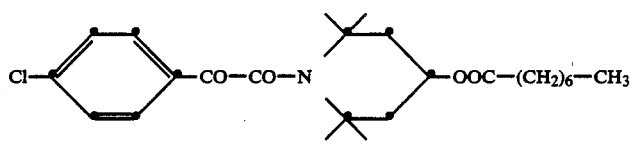

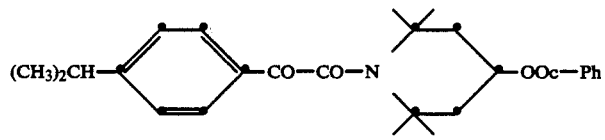

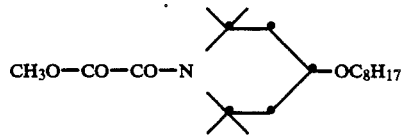

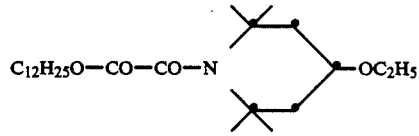

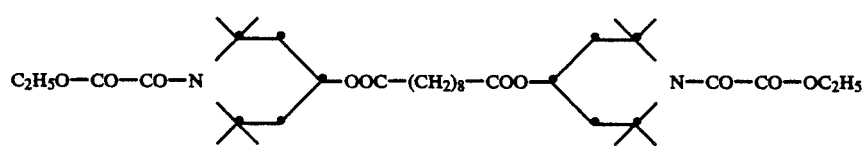
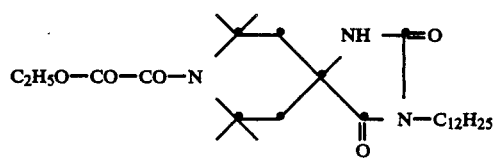
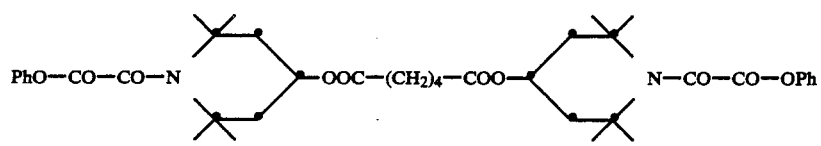
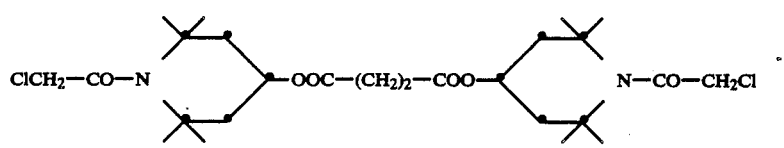
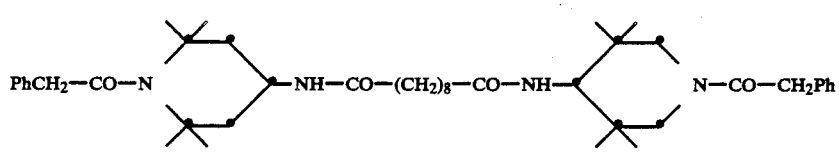
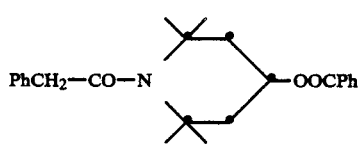
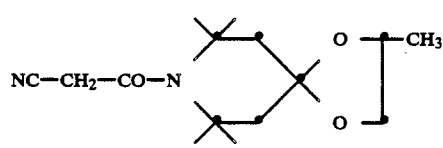
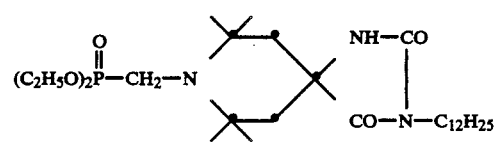
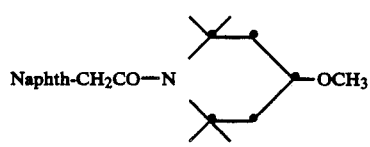
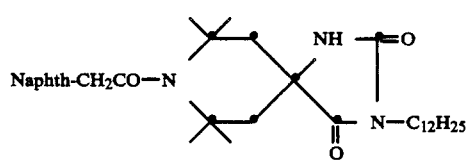

-continued
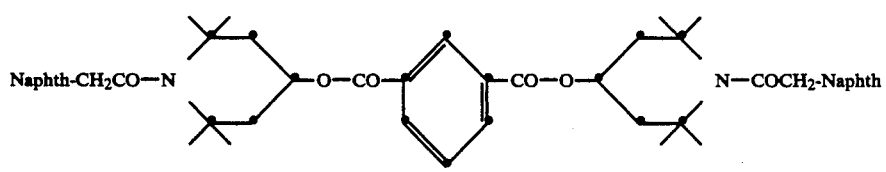
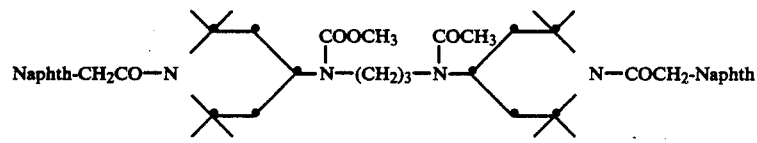
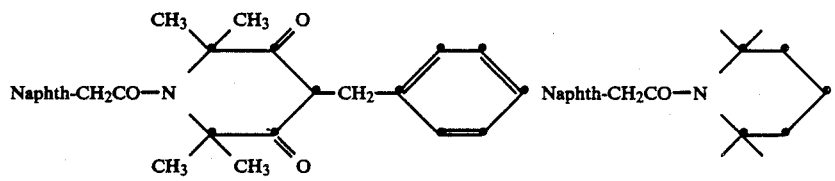
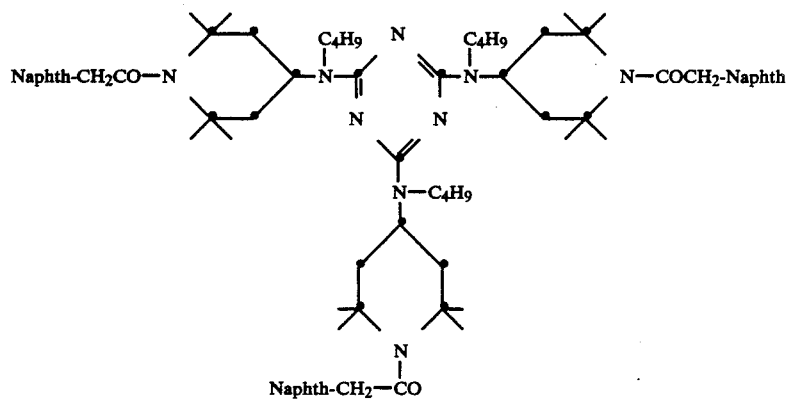
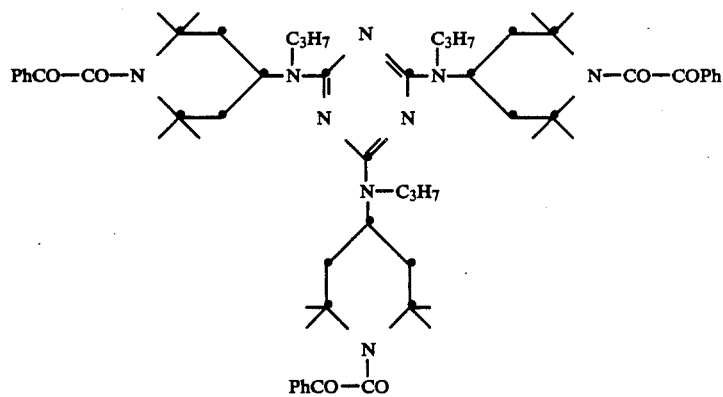
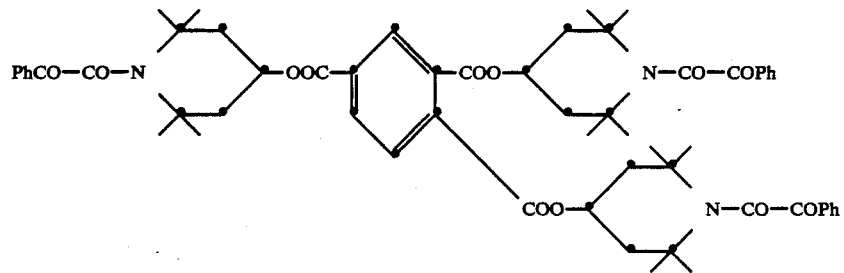

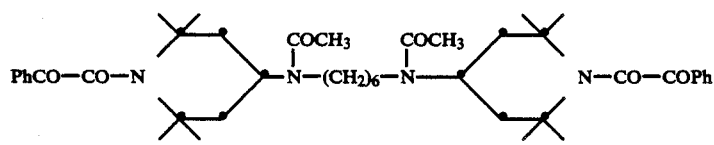
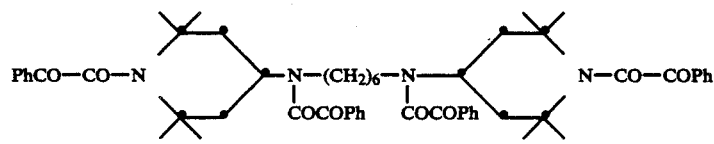
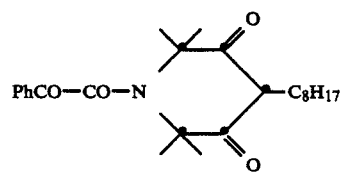
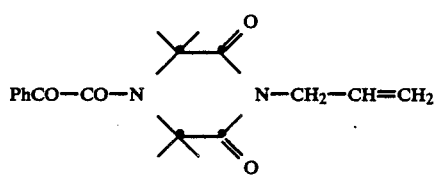
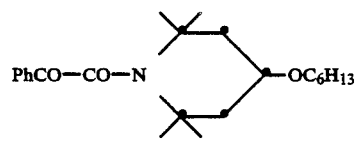
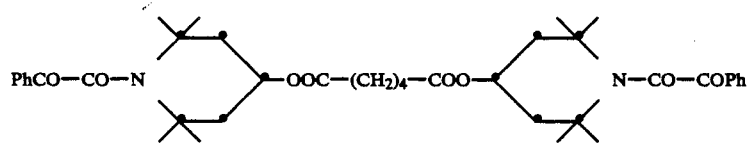
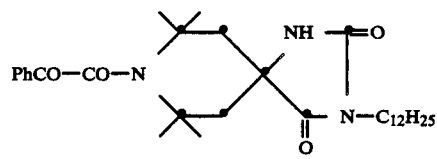
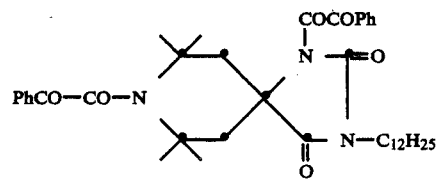
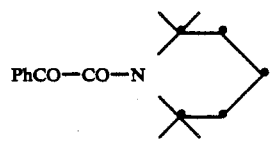
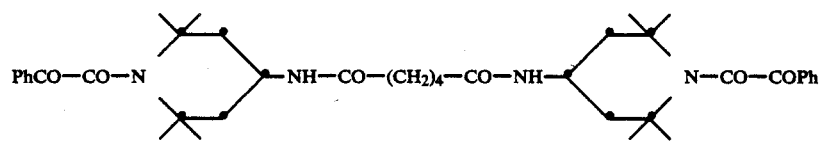

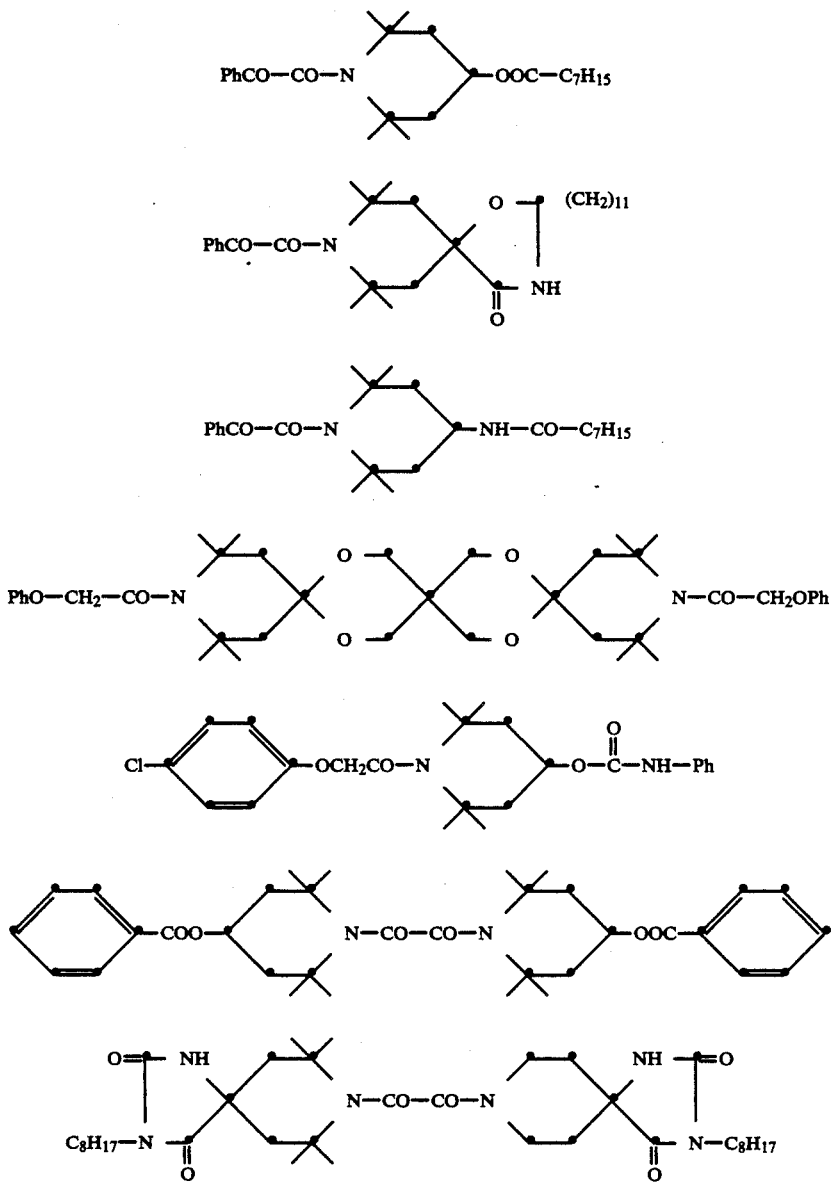

The compounds of formula I are intrinsically light stabilisers for organic polymers and can be used for stabilising them without the need for irradiation. To this end they are normally incorporated in the polymers before these are processed to moulded articles. However, they can also be added during the manufacture of the polymers. The following classes of polymer are examples of polymers which are sensitive to the action of light and which can be stabilised by addition of the compounds of this invention.

1. Polymers of mono- and diolefins, for example polyethylene (uncrosslinked or crosslinked), polypropylene, polyisobutylene, polybut-1-ene, polymethylpent-1-ene, polyisoprene or polybutadiene, and polymers of cycloolefins, e.g. of cyclopentene or norbornene.

2. Mixtures of the polymers mentioned under (1), for example mixtures of polypropylene with polyethylene or with polyisobutylene.

3. Copolymers of mono- and diolefins with each other or with other vinyl monomers, for example ethylene/propylene copolymers, propylene/but-1-ene copolymers, propylene/isobutylene copolymers, ethylene-but-1-ene copolymers, propylene/butadiene copolymers, isobutylene/isoprene copolymers, ethylene/alkylacrylate copolymers, ethylene/alkylmethacrylate copolymers, ethylene/vinyl acetate copolymers, or ethylene/acrylic acid copolymers and salts thereof (isomers), as well as terpolymers of ethylene with propylene and a diene such as hexadiene, dicyclopentadiene or ethylidene norbornene.

4. Polystyrene, poly-(p-methylstyrene).

5. Copolymers of styrene or α-methylstyrene with dienes or acrylic derivatives, for example styrene/butadiene, styrene/acrylonitrile, styrene/alkylmethacrylate, styrene/acrylonitrile/methyl acrylate, mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene/butylene/styrene, or styrene/ethylene/propylene/styrene.

6. Graft copolymers of styrene, e.g. styrene with polybutadiene, styrene and acrylonitrile with polybutadiene, styrene and maleic anhydride with polybutadiene, styrene and alkyl acrylates or alkyl methacrylates with polybutadiene, styrene and acrylonitrile with ethylene/propylene/diene terpolymers, styrene and acrylonitrile with polyalkylacrylates or polyalkylmethacrylates, styrene and acrylonitrile with acrylate/butadiene copolymers, and mixtures thereof with the copolymers listed under (5), known e.g. as ABS, MBS, ASA or AES polymers.

7. Halogen-containing polymers, e.g. polychloroprene, chlorinated rubber, chlorinated or chlorosulfonated polyethylene, especially polymers of halogenated vinyl compounds, e.g. polyvinyl chloride, polyvinylidene chloride, polyvinyl fluoride, polyvinylidene fluoride and their copolymers such as vinyl chloride/vinylidene chloride, vinyl chloride/vinyl acetate or vinylidene chloride/vinyl acetate polymers.

8. Polymers which are derived from $\alpha,\beta$-unsaturated acids and their derivatives, e.g. polyacrylates and polymethacrylates, polyacrylamides and polyacrylonitriles.

9. Copolymers of the monomers listed in (8) with one another or with other unsaturated monomers, e.g. acrylonitrile/butadiene copolymers, acrylonitrile/alkylacrylate copolymers, acrylonitrile/vinyl halide copolymers, or acrylonitrile/alkylmethacrylate/butadiene terpolymers.

10. Polymers which are derived from unsaturated alcohols and amines or their acyl derivatives or acetals, e.g. polyvinyl alcohol, polyvinyl acetate, polyvinyl stearate, polyvinyl benzoate, polyvinyl maleate, polyvinylbutyral, polyallyl phthalate, polyallyl melamine.

11. Homopolymers and copolymers of cyclic ethers such as polyethylene glycols, polyethylene oxide, polypropylene oxide or their copolymers with bisglycidyl ethers.

12. Polyacetals such as polyoxymethylene, and also those polyoxymethylenes which contain e.g. ethylene oxide as comonomer.

13. Polyphenyl oxides and polyphenyl sulfides and mixtures thereof with styrene polymers.

14. Polyurethanes which are derived on the one hand from polyethers, polyesters and polybutadienes containing hydroxy end groups, and from aliphatic or aromatic polyisocyanates on the other, as well as their precursors (polyisocyanates, polyols, prepolymers).

15. Polyamides and copolyamides which are derived from diamines and dicarboxylic acids and/or from aminocarboxylic acids or the corresponding lactams, such as polyamide 4, polyamide 6, polyamide 66, polyamide 610, polamide 11, polyamide 12, poly-2,4,4-trimethylhexamethyleneterephthalamide, poly-m-phenyleneisophthalamide, and their block copolymers with polyethers, e.g. with polyethylene glycol, polypropylene glycol or polytetramethylene glycol.

16. Polyureas, polyimides and polyamide-imides.

17. Polyesters which are derived from dicarboxylic acids and diols and/or from hydroxycarboxylic acids or the corresponding lactones, e.g. polyethylene terephthalate, polybutylene terephthalate, poly-1,4-dimethylolcyclohexane terephthalate, polyhydroxybenzoates, and also block polyether esters which are derived from hydroxylterminated polyethers.

18. Polycarbonates.

19. Polysulfones, polyether sulfones and polyether ketones.

20. Crosslinked polymers which are derived from aldehydes on the one hand and from phenols, ureas and melamines on the other hand, e.g. phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and from vinyl compounds as crosslinking agents, and also their halogen-containing modifications of low combustibility.

23. Crosslinkable acrylic resins which are derived from substituted acrylic esters, e.g. from epoxy acrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, e.g. bisglycidyl ethers, or from cycloaliphatic diepoxides.

26. Naturally occurring polymers such as cellulose, natural rubber and gelatin, and also chemically modified homologous derivatives thereof such as cellulose acetates, cellulose propionates and cellulose butyrates, and cellulose ethers such as methylcellulose.

The amount of stabiliser added is in general 0.01 to 5% by weight, preferably 0.03 to 1.5% by weight and, most preferably, 0.2 to 0.6% by weight, based on the polymer to be stabilised.

The polymers may also contain other known stabilisers, for example antioxidants, light stabilisers, metal deactivators, phosphites, thiodicarboxylates, salts of higher fatty acids or other co-stabilisers. Other modifiers conventionally employed in plastics technology may also be added, for example antistats, plasticisers, lubricants, flame retardants, pigments, reinforcing agents or fillers.

If the stabilised polymers are in the form of thin layers, as they are in the case of sheets, filaments, varnishes and coatings, the stabilisers of formula I can be cleaved photochemically by irradiation with shortwave light to form compounds which are unsubstitutsd at the sterically hindered nitrogen atom. Irradiation is preferably effected with UV light in the wavelength range from 250 to 400 nm. Suitable light sources for the irradiation are for example medium-pressure, high-pressure and low-pressure mercury lamps as well as superactinic neon tubes. At the present time a whole range of suitable devices is available, especially for continuous irradiation, in which the material to be irradiated is transported beneath the light source. The same effect is achieved when using the stabilised polymers in the open.

As mentioned at the outset, the photochemical conversion of the N-acylated stabiliser to an N-unsubstituted stabiliser is of particular importance for stabilizing acid-catalysed stoving varnishes by effecting irradiation after stoving.

Acid-curable varnishes are in particular those based on a binder that contains an amine resin, e.g. an etherified, esterified or otherwise modified melamine resin, urea resin or guanidine resin. These varnishes are normally used in admixture with alkyd, polyester or acrylic resins which contain functional groups (e.g.—OH or —COOH groups) that are crosslinked by reaction with the methylol groups of the amine resins. This crosslinking is catalysed by acids. Instead of the amine resin, the varnish can also contain methylol derivatives of polycarboximides or their ethers or esters. Sulfonic acids are usually employed as acid curing catalysts, but carboxylic acids or phosphonic acids or masked sulfonic acids are also suitable.

Acid-catalysed stoving varnishes often contain mixtures of alkyd resins, polyester resins and acrylic resins with one another or with other film-forming resins. Such film-forming resins may also be self-crosslinking, for example if they are modified by methylolamide groups, in which case they do not require the addition of an amine resin or other crosslinking agent.

The stabilisers of this invention are incorporated in the varnishes before application, preferably by adding them to a solution of the stabiliser in an organic solvent. The stoving of the varnish is usually effected in the temperature range from 100°-200° C. During stoving, the stabiliser must not volatilise and decompose. Not until the subsequent irradiation of the cured varnish coating does the photochemical cleavage of the stabilise occur.

For many finishes, especially automotive finishes, the two-coat method is employed at the present time. This method comprises applying first the pigmented varnish and then the clear varnish to the undercoat. The light stabiliser can be added to the clear varnish as well as to the pigmented varnish or to both coatings.

To obtain maximum light-resistance, the concurrent use of other conventional light stabilisers, e.g. UV absorbers or organic nickel compounds, can be advantageous. The concurrent use of UV absorbers of the 2-hydroxybenzophenone, 2-(2-hydroxyophenyl)benztriazole or oxanilide type, which may have a synergistic effect, is especially useful. Examples of such compounds are: 2-(2-hydroxy-3,5-di-tert-amylphenyl)benztriazole, 2-(2-hydroxy-5-tert-octylphenyl)benztriazole, 2-(2-hydroxy-3,5-di-tert-octylphenyl)benztriazole, 2,4-dihydroxybenzophenone, 2-hydroxy-4-octyloxybenzophenone, 2-hydroxy-4-dodecyloxybenzophenone, 2-ethyl-2-ethoxy-4'-tert-butyloxalanilide or 2-ethyl-2'-ethoxyoxalanilide.

When using such combinations, the sum of all light stabilisers is 0.2 to 5% by weight, preferably 0.5 to 2% by weight, based on the film-forming resin.

Further modifiers which may be present in the varnish are antioxidants, for example of the sterically hindered phenol derivative type, phosphorus compounds such as phosphites or phosphonites, plasticisers, levelling agents, thickeners, dispersants or bonding agents.

The following Examples illustrate the preparation of the compounds of this invention and the use thereof as stabilisers.

EXAMPLE 1

(a) 1 ml of piperidine is added to 30 g (0.2 mole) of phenylglyoxylic acid and 18.9 ml (0.26 mole) of thionyl chloride are added dropwise, with stirring, under nitrogen such that the temperature of the reaction mixture is 25°—30° C. The reaction mixture is then stirred for 24 hours at 35°-40° C. and concentrated by evaporation at a maximum temperature of 40° C. under vacuum. The residual crude phenylglyoxylyl chloride is a yellow oil containing an insignificant amount of powdery deposit. This crude product is used without further purification for the subsequent reactions.

(b) 24.1 g (0.1 mole) of 4-hexyloxy-2,2,6,6-tetramethylpiperidine are dissolved in 100 ml of absolute methylene chloride. To this solution are added 15.2 g (0.15 mole) of absolute triethylamine and the whole solution is cooled to −10° C. At this temperature a solution of 16.8 g (0.1 mole) of phenylglyoxylyl chloride in 100 ml of methylene chloride is slowly added dropwise. When this addition is complete, the reaction mixture is allowed to warm to room temperature and stirred for about 4 hours. Precipitated hydrochloride is removed by filtration and the solution is clarified by filtration over a small amount of silica gel and concentrated by evaporation, affording 28.4 g of 1-(4-hexyloxy-2,2,6,6-tetramethylpiperidino)-2-phenyl-ethane-1,2-dione as a yellow oil (stabiliser 1).

| Analysis: | theory | C = 73.96% | found | C = 73.77% |
|---|---|---|---|---|
| | | H = 9.44% | | H = 9.20% |
| | | N = 3.75% | | N = 3.25% |

Analogous reaction of phenylglyoxylyl chloride with the corresponding cyclic amines gives the following compounds:

3-dodecyl-8-(2-phenylethane-1,2-dion-1-yl)-7,7,9,9-tetramethyl-1,3,8 triazaspiro[4.5]decane-2,4-dione (stabiliser 2);

| Analysis: | theory | C = 70.82% | found | C = 70.46% |
|---|---|---|---|---|
| | | H = 9.02% | | H = 8.82% |
| | | N = 7.99% | | N = 7.96% |

3-dodecyl-1,8-bis(2-phenylethane-1,2-dione-1-yl)-7,7,9,9-tetramethyl-1,3,8-triazaspiro[4.5]decane-2,4-dions (stabiliser 3);

| Analysis: | theory | C = 71.20% | found | C = 69.82% |
|---|---|---|---|---|
| | | H = 7.81% | | H = 7.72% |
| | | N = 6.38% | | N = 6.19% | bis-[1-(2-phenylethane-1,2-dione-1-yl)-2,2,6,6-tetramethylpiperidin-4-yl]adipate, m.p. 135°-137° C. (stabiliser 4);

1-(4-benzoyloxy-2,2,6,6-tetramethlpiperidino)-2-phenylethane-1,2dione, m.p. 122°-124° C. (stabiliser 5);

1-(4-dodecyloxy-2,2,6,6-tetramethyl(piperidino)-2-phenylethane-1,2dions in the form of a yellow oil (stabiliser 6);

| Analysis: | theory | C = 76.10% | found | C = 75.78% |
|---|---|---|---|---|
| | | H = 10.35% | | H = 10.18% |
| | | N = 3.06% | | N = 2.93% |

EXAMPLE 2

Analogous reaction of ethyl oxalyl chloride ($C_2H_5OCOCOCl$) with the corresponding cyclic amines gives the following compounds:

ethyl 2-[4-hexyloxy-2,2,6,6-tetramethylpiperidino]-2-oxoacetate (stabiliser 7);

| Analysis: | theory | C = 66.82% | found | C = 66.80% |
|---|---|---|---|---|
| | | H = 10.33% | | H = 10.32% |
| | | N = 4.10% | | N = 4.07% |

3-dodecyl-8-(ethoxyoxalyl)-7,7,9,9-tetramethyl-1,3,8-triazaspiro4.5]decane-2,4-dione (stabiliser 8) of formula

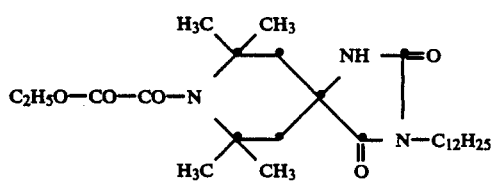

m.p. 81°-82° C.

ethyl 2-(4-benzoyloxy-2,2,6,6-tetramethylpiperidino)-2-oxoacetate (stabiliser 9);

| Analysis: | theory | C = 66.46% | found | C = 66.33% |
|---|---|---|---|---|
| | | H = 7.53% | | H = 7.56% |
| | | N = 3.88% | | N = 3.90% | cyclohexanespiro-2'-[1-(ethoxyoxalyl)-1,3-diazolidin-4-one]-5'-spirocyclohexane of formula

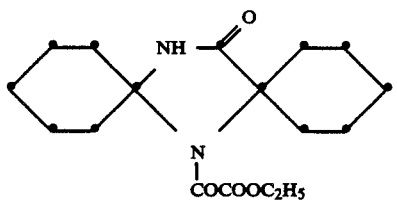

(stabiliser 10), m.p. 211°-213° C.;

bis[1-(ethoxyoxalyl)-2,2,6,6-tetramethylpiperidin-4-yl]adipate (stabiliser 11), m.p. 74°-76° C.

Analogous reaction with oxalyl chloride gives the following compounds:

oxalyl di(4-bsnzoyl-2,2,6,6-tetramethyl)piperidide

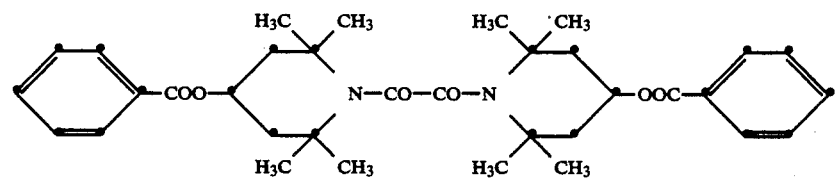

(stabiliser 12), m.p. 211°-214° C.;

1,1'-oxalyl-bis(2,2-pentamethylene-5,5-pentamethylene-1,3-diazolidin-4-one)

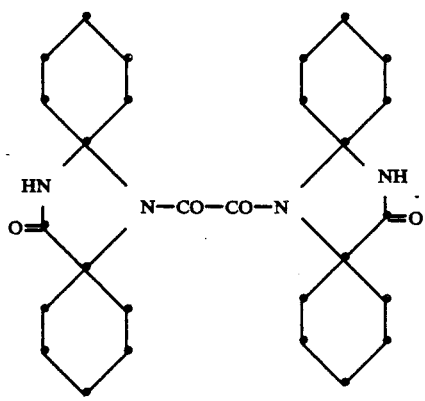

(stabiliser 13), m.p. 192°-193° C.

EXAMPLE 3

A 750 ml sulfonating flask is charged with 49.7 g (0.19 mole) of 4-benzoyloxy-2,2,6,6-tetramethylpiperidine and 25.4 g (0.1 mole) of phenylacetic anhydride. The mixture is heated under nitrogen to 150° C. and the resultant orange melt is stirred for 6 hours at this temperature. After this time, no more starting material can be detected in a thin-layer chromatogram (in ethyl acetate as eluant). The melt is allowed to cool and then dissolved in ethyl acetate. The solution is purified through a column of silica gel and concentrated by evaporation, affording a yellow resinous product (stabiliser 14) of formula

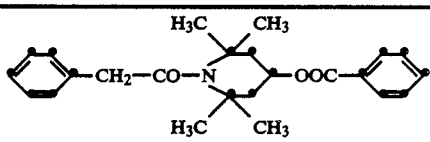

| Analysis: theory | C = 75.96% | found | C = 75.75% |
|---|---|---|---|
| | H = 7.70% | | H = 7.56% |
| | N = 3.69% | | N = 3.17% |

EXAMPLE 4

A two-layer metallic varnish is applied to aluminium sheets. The undercoat (20 μm) consists of an aluminium-pigmented varnish based on a polyester/cellulose acetobutyrate/melamine resin mixture. A clear varnish (40 μm) based on a hydroxylated acrylic resin (Macrynal®SM 510 N, ex Hoechst AG) and a polyisocyanate (Desmodur®N 75, ex Bayer AG) is applied as topcoat. A solution of a stabiliser listed in Table 1 in a 1:1 mixture of ethylene glycol/xylene is added to the clear varnish. For curing, the samples are heated to 80° C. for 45 minutes.

The samples are subjected to solar radiation in Florida (5° south) and the surface gloss is measured at 6 month intervals in accordance with ASTM Test Method D 523. An unstabilised sample of the same varnish serves as comparison.

TABLE 1

| Stabiliser | 20° Gloss (%) after | | | | |
|---|---|---|---|---|---|
| | 0 | 6 | 12 | 18 | 24 months |
| none | 96 | 84 | 81 | 59 | 43 |
| 1% of 2 | 96 | 87 | 84 | 78 | 73 |
| 2% of 2 | 96 | 84 | 84 | 80 | 79 |
| 2% of 3 | 96 | 87 | 87 | 81 | 77 |

EXAMPLE 5

Samples are prepared using a two-layer metallic stoving varnish comprising an undercoat (20 μm) of an aluminium-pigmented polyester/cellulose acetobutyrate/melamine resin varnish and a topcoat of a clear varnish (40 μm) based on a thermosetting acrylic resin (Viacryl ® VC 373, ex Vianova) and a melamine resin (Maprenal ® MF 590, ex Hoechst AG) as crosslinking agent. A stabiliser listed in Table 2 is added to the acrylic resin. The samples are stoved for 30 minutes at 130° C.

The samples are exposed in a Xenotest 1200 weathering device and the 20° gloss is measured at intervals of 800 hours in accordance with DIN 67 530. The results are reported in Table 2.

TABLE 2

| Stabiliser | 20° Gloss (%) after |   |   |   |   |   |
|---|---|---|---|---|---|---|
|  | 0 | 800 | 1600 | 2400 | 3200 | 4000 h |
| none | 81 | 53 | 26 | 20 | — | — |
| 1% of 5 | 87 | 65 | 52 | 35 | 23 | 19 |
| 1% of 6 | 88 | 77 | 55 | 42 | 31 | 26 |

Noticeable cracks occur in the samples without stabiliser after 2800 hours exposure to weathering, whereas cracks do not appear in the stabilised samples until after 5200 hours exposure.

What is claimed is:

1. An organic polymer stabilised against the adverse action of actinic light, which polymer contains 0.1 to 5% by weight, of a compound of formula I $$\left[ A-\overset{O}{\underset{\|}{C}} \right]_m B \quad (I)$$

wherein
m is 1, 2 or 3,
A is a $R^1$—CO— or $R^2$-CH$_2$-group, wherein
  $R^1$ is phenyl or phenyl which is substituted by halogen, $C_1$-$C_{12}$alkyl or $C_1$-$C_4$alkoxy or is unsubstituted naphthyl and
  $R^2$ is —CN or CH$_3$CO; and
when m is 1,
B is a radical corresponding to the formulae (II)

(III)

wherein
$R^5$ is hydrogen, —OR$^8$, $$-O-\overset{O}{\underset{\|}{C}}-R^9, \quad -O-\overset{O}{\underset{\|}{C}}-NH-R^{10},$$

—N($R^{10}R^{11}$),
$R^6$ is —OH or —OR$^{12}$ and $R^7$ is —OR$^{12}$, —CN, —COOR$^{13}$ or —CONH$_2$, or
$R^6$ and $R^7$ together are the oxo radical (=O), or $R^6$ and $R^7$, together with the C-atom to which they are attached, form an unsubstituted 2-spiro-1, 3-dioxolane, 2-spiro-1,3-dioxane, 5-spiro-1, 3-oxazolidine, 2-spiro-1,3-oxazolidine or 5-spiro-1,3-imidazolidine ring or said ring substituted by one or more identical or different members selected from $C_1$-$C_{12}$alkyl or the oxo radical,
$R^8$ is $C_1$-$C_{12}$alkyl, benzyl, allyl or 2-cyanoethyl,
$R^9$ is $C_1$-$C_{18}$alkyl, $C_2$-$C_{12}$alkenyl, $C_5$-$C_8$cycloalkyl, phenyl or phenyl which is substituted by halogen, $C_1$-$C_{12}$alkyl, $C_1$-$C_4$ alkoxy or hydroxyl, or is $C_7$-$C_{12}$phenylalkyl, $C_1$-$C_4$ alkoxy or phenoxy,
$R^{10}$ is $C_1$-$C_{12}$ alkyl, cyclohexyl, phenyl, naphthyl, or phenyl which is substituted by $C_1$-$C_4$alkyl,
$R^{11}$ is $C_2$-$C_{12}$alkanoyl, $C_3$-$C_8$alkenoyl, benzoyl or a group of the formula wherein $R^{14}$ and $R^{15}$ are each independently of the other $C_1$-$C_8$alkoxy, phenoxy, or a group —N($R^{10}$)($R^{16}$), in which $R^{16}$ is hydrogen or $C_1$-$C_{12}$alkyl,
$R^{12}$ is $C_1$-$C_{12}$alkyl and $R^{13}$ is $C_1$-$C_4$alkyl, and
Y is hydrogen, $C_1$-$C_{12}$alkyl, allyl or benzyl;
when m is 2,
B is a divalent radical corresponding to the formulae (IV)

-continued

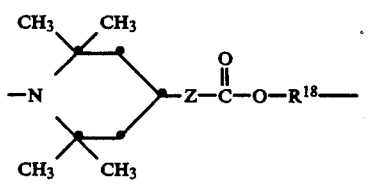

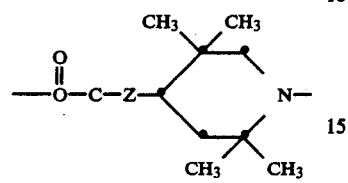

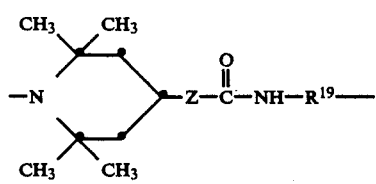

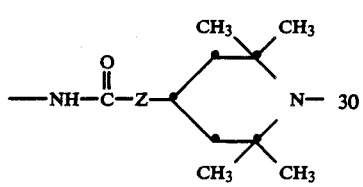

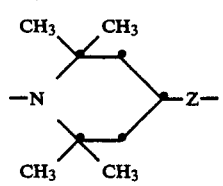

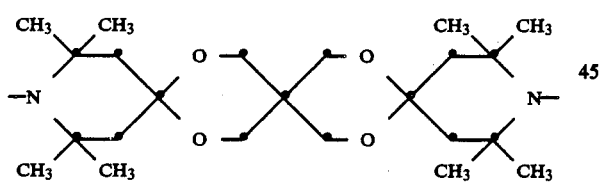

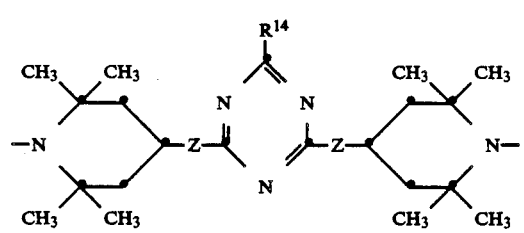

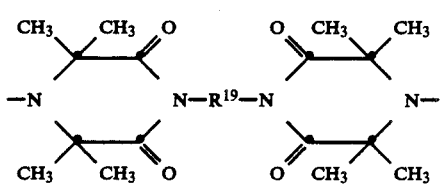

-continued

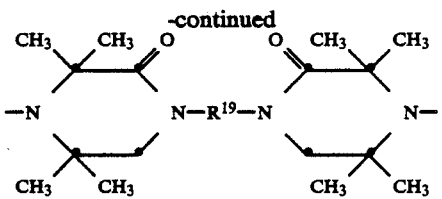

wherein
Z is —O—, —NH— or —NR$^{10}$—,
R$^{17}$ is methylene, 1,2-ethylene, C$_3$–C$_{20}$polymethylene, or branched C$_3$–C$_{20}$alkylene, C$_2$–C$_{10}$alkenylene, 1,4-cyclohexylene, 1,3-cyclohexylene, cyclohexane-1,4-dimethylene, 1,3- or 1,4-phenylene, 1,4- or 1,5-naphthylene, 4,4,-diphenylene, diphenylmethane-4,4'-diyl, diphenyl oxide-4,4'-diyl or m- or p-xylene, or a radical —NH—R$^{19}$—NH—,
R$^{18}$ is 1,2-ethylene, 1,2-propylene, 1,3-propylene, 1,2-butylene, 1,4-butylene, hexamethylene, 1,4-cyclohexylene or cyclohexane-1,4-dimethylene,
R$^{19}$ is 1,2-ethylene, trimethylene, tetramethylene, hexamethylene, octamethylene, dodecamethylene, 2,2-dimethyltrimethylene, trimethyloctamethylene, 1,4-cyclohexylene, cyclohexane-1,4-dimethylene, 1,3-phenylene, 4,4'-diphenylene, diphenylmethane-4,4'-diyl, diphenyl oxide-4,4 -diyl, or m- or p-xylene, and
R$^{10}$ and R$^{14}$ are as defined above; and, when m is 3, B is a trivalent radical corresponding to the formulae

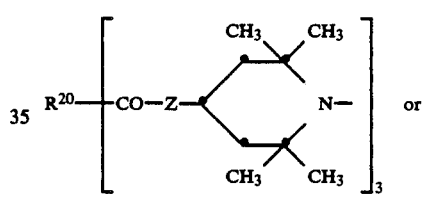 or

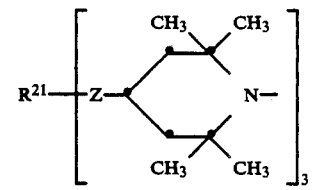

wherein
R$^{20}$ is propane-1,2,3-triyl, butane-1,2,4-triyl, benzene-1,3,5-triyl, benzene-1,2,4-triyl or naphthalene-1,4,5-triyl, R$^{21}$ is a 1,3,5-triazin-2,4,6-triyl radical and Z is as defined above.

2. A stoving varnish containing an acid curing catalyst and a compound of formula I as defined in claim 1.

3. An acid catalysed stoving varnish according to claim 2, which additionally contains a UV absorber of the 2-hydroxybenzophenone, 2-(2-hydroxyphenyl)benzotriazole or oxanilide type.

4. A method of stabilizing an organic polymer against light-induced damage by incorporation of a light stabiliser, which comprises adding to said polymer 0.01 to 5% by weight of a compound of formula I of claim 1 and subsequently irradiating said polymer with shortwave light.

5. The method of claim 4, wherein said organic polymer is an acid-catalyzed stoving varnish and said irradiation is conducted subsequent to stoving.

6. The composition according to claim 1, wherein A is a benzoyl group.

* * * * *